(12) United States Patent
Mostafavi et al.

(10) Patent No.: US 7,177,386 B2
(45) Date of Patent: Feb. 13, 2007

(54) BREATHING SYNCHRONIZED COMPUTED TOMOGRAPHY IMAGE ACQUISITION

(75) Inventors: Hassan Mostafavi, Los Altos, CA (US); Edward J. Seppi, Portola Valley, CA (US); Larry Partain, Los Altos, CA (US)

(73) Assignee: Varian Medical Systems Technologies, Inc., Palo Alto, CA (US)

( * ) Notice: Subject to any disclaimer, the term of this patent is extended or adjusted under 35 U.S.C. 154(b) by 73 days.

(21) Appl. No.: 10/801,947

(22) Filed: Mar. 15, 2004

(65) Prior Publication Data

US 2005/0201509 A1   Sep. 15, 2005

(51) Int. Cl.
*H05G 1/00* (2006.01)
(52) U.S. Cl. .............................................. 378/4; 378/8
(58) Field of Classification Search ..................... 378/4, 378/8, 95, 15, 19
See application file for complete search history.

(56) References Cited

U.S. PATENT DOCUMENTS

| 3,952,201 A | 4/1976 | Hounsfield |
| 5,265,142 A | 11/1993 | Hsieh |
| 6,269,140 B1 * | 7/2001 | Takagi et al. ................... 378/8 |
| 2004/0081269 A1 * | 4/2004 | Pan et al. ....................... 378/4 |

OTHER PUBLICATIONS

International Search Report dated Dec. 1, 2005 (Pct/US05/08037)

* cited by examiner

*Primary Examiner*—Edward J. Glick
*Assistant Examiner*—Irakli Kiknadze
(74) *Attorney, Agent, or Firm*—Bingham McCutchen LLP (57) ABSTRACT

A method for collecting computed tomography (CT) image data includes determining a number of intervals N into which a respiratory cycle is to be divided, determining a number of respiratory cycles M to be covered in one gantry rotation, and rotating a gantry to collect at least M×N sets of CT image data of at least a portion of a patient, wherein each set of the CT image data corresponds to a phase of a respiratory cycle.

57 Claims, 10 Drawing Sheets

BREATHING SYNCHRONIZED COMPUTED TOMOGRAPHY IMAGE ACQUISITION

BACKGROUND OF THE INVENTION

1. Field of the Invention

This invention relates generally to systems and methods for image acquisition and, more specifically, to systems and methods for collecting computed tomography (CT) image data and reconstructing CT images.

2. Background of the Invention

Computed tomography is an imaging technique that has been widely used in the medical field. In a procedure for computed tomography, an x-ray source and a detector apparatus are positioned on opposite sides of a portion of a patient under examination. The x-ray source generates and directs a x-ray beam towards the patient, while the detector apparatus measures the x-ray absorption at a plurality of transmission paths defined by the x-ray beam during the process. The detector apparatus produces a voltage proportional to the intensity of incident x-rays, and the voltage is read and digitized for subsequent processing in a computer. By taking a plurality of readings from multiple angles around the patient, relatively massive amounts of data are thus accumulated. The accumulated data are then analyzed and processed for reconstruction of a matrix (visual or otherwise), which constitutes a depiction of a density function of a volume of the bodily region being examined. By considering one or more sections in the volume, a skilled diagnostician can often diagnose various bodily ailments such as tumors, blood clots, etc.

Computed tomography has found its principal application to examination of bodily structures or the like which are in a relatively stationary condition. However, currently available computed tomographic apparatus may not be able to generate tomographic images with sufficient quality or accuracy due to physiological movement of a patient. For example, beating of a human heart and breathing have been known to cause degradation of quality in CT images. U.S. Pat. No. 3,952,201 issued to Hounsfield, describes a system that compensates for a blurring of a radiograph due to heart motions by collecting image data of a patient at different angles while monitoring the patient's heart. The image data and the heart motion data are then correlated in a computer, and image data that was obtained when the heart's motion exceeded a threshold level is rejected. However, such method does not generate desirable CT images for a portion of a cardiac cycle when the heart's motion exceeds the threshold level.

Degradation of quality of CT images due to patient's breathing is more difficult to address than that associated with heart motion. Patients' breathing poses a unique problem to CT imaging that is different from heart motion. This is because the pattern and the period of a patient's breathing cycle is generally less consistent when compared to those of the patient's cardiac cycle. As such, while a particular phase of a cardiac cycle may be predicted with sufficient accuracy, a particular phase of a breathing cycle may not be as easily predicted or determined.

Furthermore, there has been an increased desire to visualize organ motion by viewing a sequence of CT images as a movie sequence. However, collecting a large quantity of CT image data sufficient for forming a video while considering breathing motion may take a much longer time. This may cause a patient who is confined within a gantry opening to feel uncomfortable and subject the patient to excessive radiation.

SUMMARY OF THE INVENTION

A method for collecting CT image data includes determining a number of intervals N into which a respiratory cycle is to be divided, determining a number of respiratory cycles M to be covered in one gantry rotation, and rotating a gantry to collect at least M×N sets of CT image data of at least a portion of a patient, wherein each set of the CT image data corresponds to a phase of a respiratory cycle. In some embodiments, the method further includes repeating the step of rotating until the number of gantry rotation is at least N. The method provides a systematic process for collecting CT image data such that a complete set of data for CT image reconstruction can be collected efficiently while considering a patient's breathing.

In one embodiment, the gantry rotation speed is maintained constant as CT image data are collected. In this case, while the gantry is rotating about the patient, a physiological gating system records motion data associated with the breathing of the patient. The collected CT image data are time-stamped to be synchronized with the recorded motion data at a later time. In one embodiment, while CT image data are being collected, breathing instruction may be given to the patient. This has the benefit of ensuring that the breathing phases of the patient approximately matches with the phases of the gantry rotation.

In another embodiment, the gantry rotation speed is adjusted as CT image data are collected such that a gantry phase approximately matches with a corresponding phase of the patient. The adjustment of the gantry rotation speed can be performed based on a difference between a gantry phase and a detected breathing phase of the patient, or alternatively, based on a difference between a gantry phase and a predicted breathing phase of the patient. In one embodiment, the rate of CT image data collection is constant regardless of the speed of the gantry rotation. In another embodiment, the rate of CT image data collection is adjusted in response to the speed of the gantry rotation.

A method for generating a CT image includes collecting data samples representative of a physiological movement of a patient due to breathing, determining a number of intervals N into which a breathing cycle of the patient is to be divided, rotating a gantry at least N times to acquire image data of at least a part of the patient, gathering image data acquired at a same phase of a breathing cycle, and generating a CT image using the gathered image data. The generated CT images can be displayed in a sequence to form a video.

Other aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how advantages and objects of the present invention are obtained, a more particular description of the present invention briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

Various embodiments of the present invention are described hereinafter with reference to the figures. It should be noted that the figures are not drawn to scale and elements of similar structures or functions are represented by like reference numerals throughout the figures. It should also be noted that the figures are only intended to facilitate the description of specific embodiments of the invention. They are not intended as an exhaustive description of the invention or as a limitation on the scope of the invention. In addition, an aspect described in conjunction with a particular embodiment of the present invention is not necessarily limited to that embodiment and can be practiced in any other embodiments of the present invention.

Figure 1:
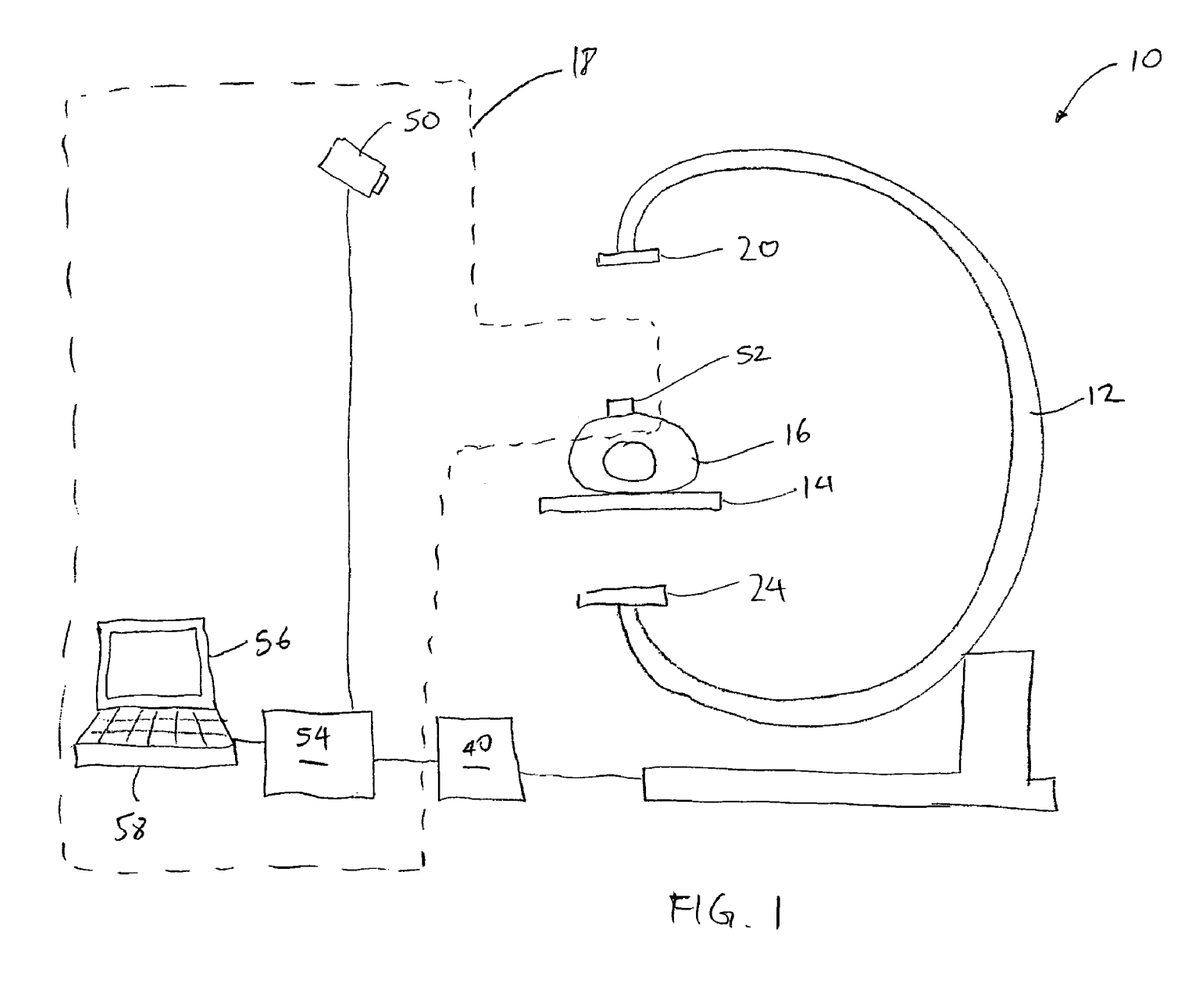
FIG. 1 illustrates a computed tomography system in which embodiments of the present invention may be implemented.

Referring now to the drawings, in which similar or corresponding parts are identified with the same reference numeral, FIG. 1 illustrates a computed tomography image acquisition system 10 in accordance with an embodiment of the present invention. The system 10 includes a gantry 12, a panel 14 for supporting a patient 16, and a position monitoring system 18. The gantry 12 includes an x-ray source 20 that projects a beam of x-rays towards a detector 24 on an opposite side of the gantry 12 while the patient 16 is positioned at least partially between the x-ray source 20 and the detector 24. By means of non-limiting examples, the beam of x-rays can be a cone beam or a fan beam. The detector 24 has a plurality of sensor elements configured for sensing a x-ray that passes through the patient 16. Each sensor element generates an electrical signal representative of an intensity of the x-ray beam as it passes through the patient 16.

During a scan to acquire x-ray projection data (i.e., CT image data), the gantry 12 rotates about the patient 16 while the position monitoring system 18 monitors a position of at least a portion of the patient 16. In the illustrated embodiment, the position monitoring system 18 includes an optical device 50, a marker block 52, and a processor 54. The position monitoring system 18 may also include a monitor 56 for displaying data and an input device 58, such as a keyboard or a mouse, for inputting data. The processor 54 is coupled to the optical device 50 and a gantry rotation control 40. The rotation of the gantry 12 and the operation of the x-ray source 20 are controlled by the gantry rotation control 40, which provides power and timing signals to the x-ray source 20 and controls a rotational speed and position of the gantry 12 based on signals received from the optical device 50 or the processor 54. Although the control 40 is shown as a separate component from the gantry 12 and the processor 54, in alternative embodiments, the control 40 can be a part of the gantry 12 or the processor 54.

Figure 2A:
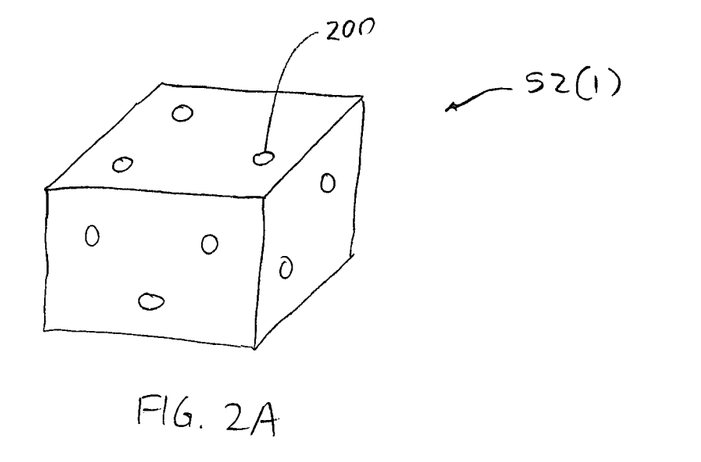
FIGS. 2A–2C shows marker blocks in accordance with various embodiments of the present invention.
Figure 2B:
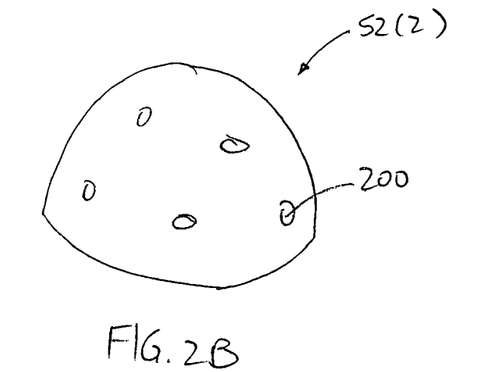
Figure 2C:
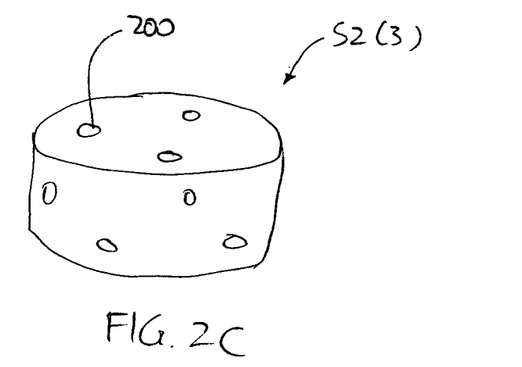

The optical device 50 may be a camera or other imaging devices, and is configured to sense an image of the marker block 52. The marker block 52 preferably comprises a reflective or retro-reflective material than can reflect light, whether in the visible or invisible wavelengths. FIG. 2A depicts an embodiment of a marker block 52(1) having a rectangular shape with multiple reference locations comprised of retro-reflective elements 200 located on its surface. FIG. 2B depicts an alternate marker block 52(2) having a hemispherical shape comprised of a plurality of retro-reflective elements 200 attached to its surface. FIG. 2C depicts another alternate marker block 52(3) having a disk shape. Marker block having other shapes may also be used so long as the size, spacing, and position of the reference locations are configured such that the optical device 50 can view and generate an image that accurately shows the positioning of the marker block 52.

When using the position monitoring system 18, one or more marker block 52 is placed on or secured to the patient 16, and the optical device 50 is used to sense the marker block 52. The optical device 50 produces a set of image coordinates for the marker elements 200 on the marker block 52. The position and distance of the marker elements 200 located on the marker block 52 is known relative to other marker elements 200 on the same marker block 52. By comparing the position and distance between the marker elements 200 on a recorded image frame with a reference position and image stored for the position monitoring system 18, the absolute position and orientation of the marker block 52 can be determined with a high degree of accuracy. This, in turn, provides an accurate position and orientation estimation for the patient position or the patient body position upon which the marker block 52 is attached. Such and similar physiological gating systems have been described in U.S. patent application Ser. No. 09/893,122, filed Jun. 26, 2001, the entire disclosure of which is expressly incorporated by reference herein.

Utilizing a video or optical based system for determining patient body position is advantageous in that it provides a reliable mechanism for repeating measurement results between uses on a given patient. In addition, such technique is noninvasive and no cables or connections must be made to the patient 16. Moreover, if use of the marker block 52 is impractical, the system can still be utilized without marker block 52 by performing measurements of physiological activity keyed to selected body landmarks. Finally, such method is more accurate because it is based upon absolute measurement of external anatomical physical movement. The position monitoring system 18 is desirable for monitoring physiological movement due to breathing, the pattern and period of which are less predictable or consistent than those associated with cardiac movement.

Figure 3:
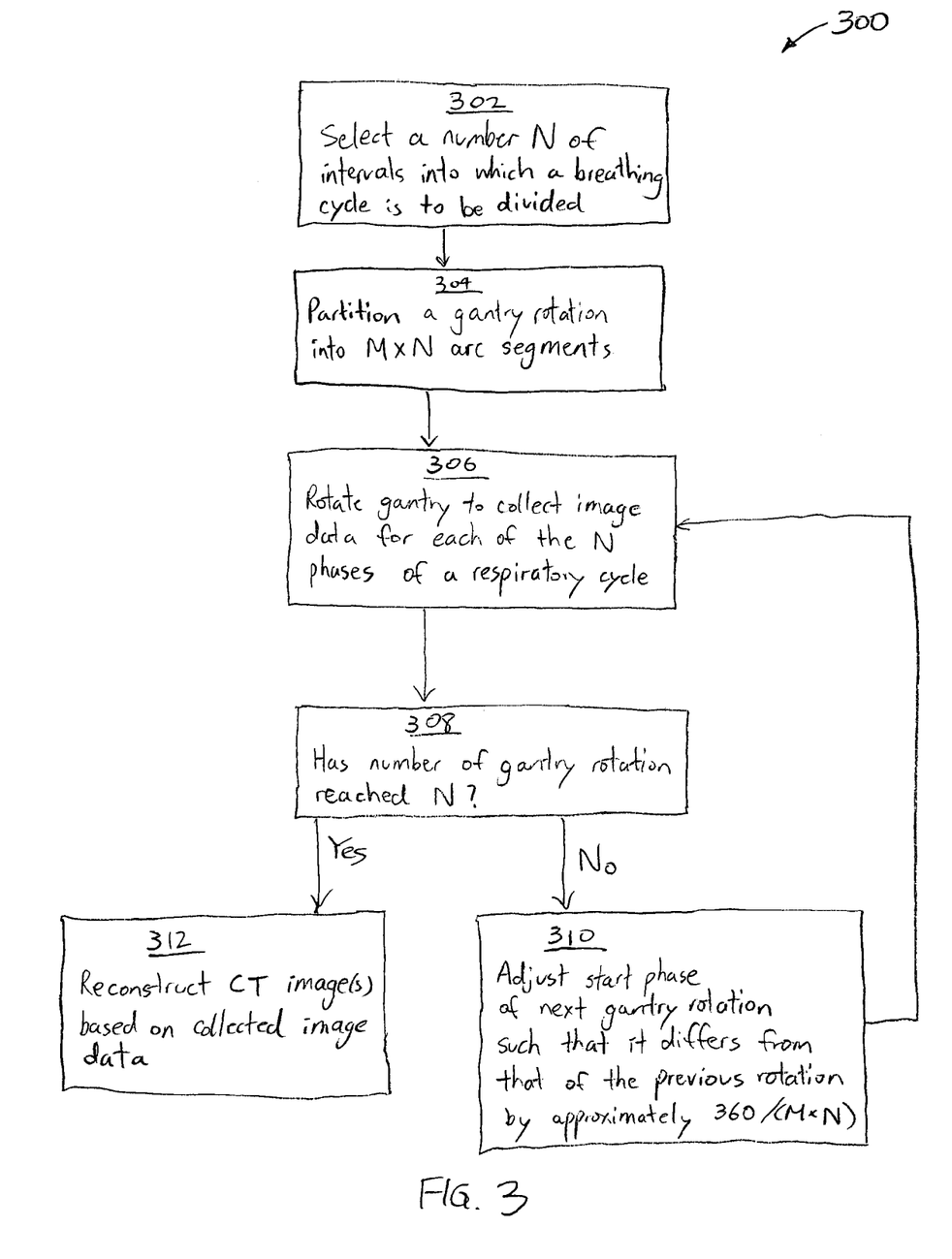
FIG. 3 is flowchart showing a process for collecting computed tomography image data in accordance with an embodiment of the present invention.

FIG. 3 shows a method 300 for collecting CT image data in accordance with an embodiment of the present invention.

First, a user selects a number of intervals N into which a breathing cycle is to be divided (Step 302). For the purpose of illustration, it will be assumed that N=3, and the corresponding N phases of the breathing intervals are 120°, 240°, and 360° (or 0°). However, the respiratory cycle can also be divided into other number of intervals, depending on the particular application. Generally, the more the number of intervals N into which a respiratory cycle is divided, the more CT images can be reconstructed in a respiratory cycle, and the smoother the transition between the frames when the CT images are displayed in a sequence (as in a video).

Figure 4:
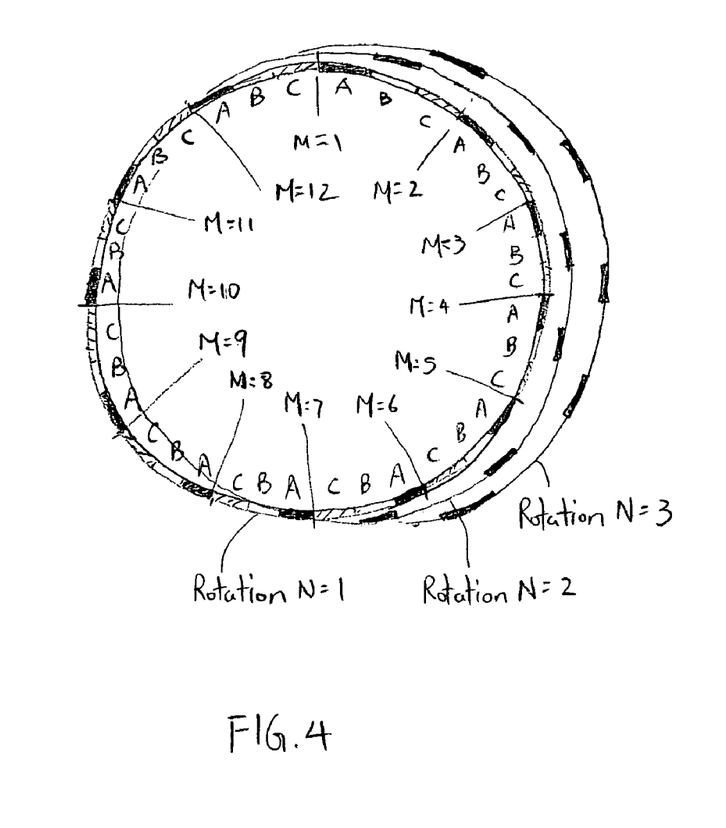
FIG. 4 illustrates rotations of a gantry, particularly showing each gantry rotation partitioned into arc segments.
Figure 5:
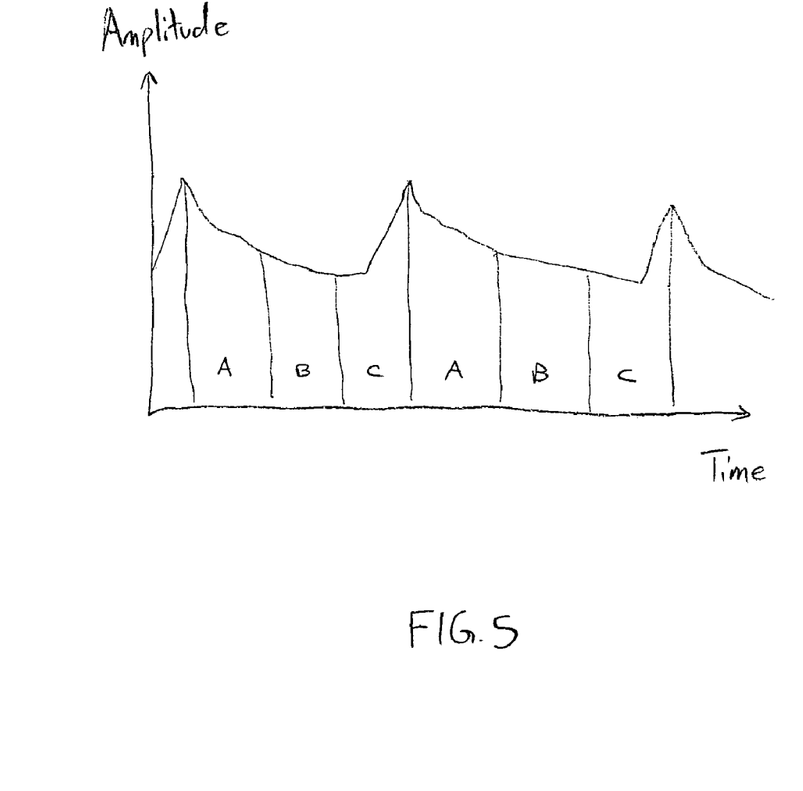
FIG. 5 is a motion signal chart, particularly showing breathing cycles divided into a number of intervals.

Next, a gantry rotation is partitioned into M×N arc segments or sequences, where M is at least equal to a minimum gantry rotation period $T_{min}$ divided by an average breathing period $T_b$ (i.e., $M \geq T_{min}/T_b$) (Step 304). As such, M represents a number of respiratory cycles that can be covered by one gantry rotation. In one embodiment, M is determined by rounding $T_{min}/T_b$ up to the nearest integer. For example, assuming $T_b$=5 seconds, if the fastest speed of gantry rotation is 62 seconds per revolution, then $T_{min}$=62 seconds, and M=13. The average breathing period $T_b$ may be determined using the system 18. FIG. 4 shows an example of a diagram of a gantry rotation which is divided into 36 arc segments (with M=12 and N=3). The three intervals (corresponding to N=3) of the breathing cycle are referenced as "A", "B", and "C", respectively. FIG. 5 is a breathing signal chart, showing each breathing cycle divided into N=3 intervals, and the corresponding intervals A, B, and C.

Next, the gantry 12 is caused to rotate about the patient 16 to collect CT image data while the position monitoring system 18 monitors a breathing motion of the patient 16 (Step 306). During the gantry rotation, the system 10 collects M×N sets of image data, with each set corresponding to a phase of a respiratory cycle.

In one embodiment, the gantry 12 rotates about the patient 16 at a constant speed and systematically collect CT image data. While the gantry 12 is rotating about the patient 16, the position monitoring system 18 records motion data associated with the breathing of the patient 16. The collected CT image data are time-stamped such that they can be synchronized with the recorded motion data at a later time. In one embodiment, while the system 10 is collecting CT image data, breathing instruction may be given to the patient 16. This has the benefit of ensuring that the breathing phases of the patient 16 approximately matches with the arc segments of the gantry rotation.

In another embodiment, the gantry 12 does not rotate about the patient 16 at a constant speed, but adjusts its speed based on a detected phase of a breathing cycle. In this case, as the gantry rotates about the patient 16, the position monitoring system 18 monitors the breathing behavior of the patient 16, and determines a phase of a respiratory cycle based on a detected position of the marker block 52 on the patient 16. The processor 54 then determines whether a position of the gantry 12 (i.e., the gantry phase) matches with the prescribed phases associated with the divided intervals of the breathing cycle—i.e., whether an arc segment of the gantry rotation matches with its associated phase of the breathing cycle. If the gantry phase is "behind" a corresponding phase of a breathing cycle, the processor 54 then increases the speed of the gantry 12 such that subsequent arc segments can match up with their corresponding phases of a breathing cycle. If the gantry phase is "ahead" of a corresponding phase of a breathing cycle, the processor 54 then decreases the speed of the gantry 12. As such, the gantry rotation speed is controlled such that the gantry rotation is partitioned into M×N number of arc segments, with each arc segment corresponding to a phase of a breathing cycle.

In one embodiment, the system 10 adjusts (increases or decreases) the speed of the gantry 12 by a prescribed increment, and repeats the adjustment until the gantry phase matches with a detected phase of a breathing cycle of the patient 16. In another embodiment, the amount of speed adjustment for the gantry 12 is based on a difference between the gantry phase and the detected breathing phase. In this case, the more the difference between the gantry phase and the detected breathing phase, the more speed adjustment is prescribed to the gantry 12. In yet another embodiment, the amount of speed adjustment for the gantry 12 is based on a predicted phase of a respiratory cycle. In this case, the processor 54 performs pattern matching and detects repetitiveness on the collected motion data to estimate a next phase of a breathing cycle. Based on the current gantry rotation speed, the processor can determine a gantry phase at a future point in time, and estimates a difference between a future gantry phase and the estimated next breathing phase of the patient 16. The processor 54 then determines how much the gantry 12 needs to increase or decrease in its speed to compensate for the difference. A method of predictively estimating a phase of a physiological cycle will be described below.

It should be noted that during a gantry rotation, 800–1500 projection data can be obtained, depending on the speed of the gantry rotation and the collection rate of CT image data. In one embodiment, the rate of CT image data collection remains constant regardless of the speed of the gantry rotation. In another embodiment, the rate of CT image data collection may be increased or decreased in response to the changing speed of the gantry rotation such that a uniform angular separation is maintained between acquired projections. For example, if the gantry 12 at a current phase is rotating twice as fast as the previous phase, the CT image data collection rate for the current phase may be reduced by half as that for the previous phase. This has the benefit of obtaining a relatively more uniform angular distribution of data during the gantry rotation.

Returning to FIG. 3, the processor 54 next determines whether the number of gantry rotation performed has reached N (step 308). If the number of gantry rotation has not reached N, then the gantry 12 is caused to rotate additional revolution(s) until the number of gantry rotation performed has reached N. The starting phase of each gantry rotation is preferably differ by approximately 360/(M×N), thereby allowing 360° of coverage for each of the N phases of a physiological cycle. As shown in FIG. 4, the second rotation of the gantry 12 is modulated to offset the arc segments of the second gantry rotation from the corresponding arc segments of the first gantry rotation such that the arc segments of the second gantry rotation completes a portion of the complete gantry phase (i.e., 360°) not covered by the first gantry rotation. Similarly, the third rotation of the gantry 12 is modulated to offset the arc segments of the third gantry rotation from the corresponding arc segments of the second gantry rotation such that the arc segments of the third gantry rotation completes a portion of the complete gantry phase not covered by the first and second gantry rotations. Note that not all of the arc segments are shown for the second and third gantry rotations for clarity. As such, for a given breathing phase interval, with proper gantry angle control in consecutive rotations, the arc segments of each gantry rotation can be aligned in such a manner that sufficient projection images can be made available for CT image reconstruction.

In an alternative embodiment, the starting phase of each gantry rotation is differ by less than 360/(M×N) to thereby allow some overlapping of image data for each phase of a respiratory cycle. In this case, the number of gantry rotations needed to provide a 360° coverage for each of the N respiratory intervals is at least N+1. It should be noted that the number of gantry rotations should not be limited to N or N+1 as discussed previously, and that the processor 54 can cause the gantry 12 to make additional rotation(s) in order to obtain additional image data needed for CT image reconstruction. The additional rotation could also be used to fill any "gaps" caused by patient coughing, or other patient movements. As used in this specification, a "gap" is defined as an image with no valid phase because of an absence of periodicity.

It should be noted that the number of gantry rotations should not be limited to those discussed previously, and that the gantry 12 can make other numbers of rotation. For example, in some embodiments, instead of making N rotations, the gantry 12 can rotate less than N times. In such cases, the method does not provide a 360° coverage for each of the N respiratory intervals. However, CT images can still be reconstructed using the CT image data collected. Also, in other embodiments, the gantry 12 can rotate more than N times until a desired number of CT image data are collected.

In other embodiments, instead of collecting CT image data for each of the N phases of a breathing cycle, CT image data are collected only for a desired phase range of a breathing cycle. For example, a breathing cycle may be divided into N=3 intervals, but CT image data may be desired to be collected for only the first ⅓ of a breathing cycle. In some embodiments, CT image data are collected during the first ⅓ of a breathing cycle. After the first ⅓ of a breathing cycle, the gantry 12 stops rotating to wait for a next desired respiratory interval (i.e., the next first ⅓ of a breathing cycle), and starts rotating when the next desired phase of a breathing cycle occurs (or is predicted to occur). As such, in the example, the gantry 12 only rotates once to provide a 360° coverage for a prescribed phase range of a breathing cycle. As can be seen from the example, by prescribing image data to be collected for certain phase range of a breathing cycle, the gantry 12 can make less than N rotations to provide coverage for the prescribed phase range. Other similar methods can be used. In general, the gantry can be stopped, slowed or speeded for portions of a rotation to get to a desired location at a desired time. For example, in some embodiments, a number of rotations greater than one but less than the number of respiratory phases can be used by, for example, capturing data for a desired phase or phases when the gantry is in the desired position for such phase(s). During other phases, the gantry can be stopped, slowed or speeded so that in the subsequent portion of the current rotation and/or in one or more subsequent rotations it is in the desired position to capture data for the phase(s) of interest from locations that weren't captured in previous rotation(s). Moreover, in some cases, fewer rotations can be used by foregoing having data for the entire 360° coverage for the phase(s) of interest and instead having data for such phase(s) from a sufficient number of angles to produce an image of sufficient quality for the purpose at hand.

If the number of gantry rotation has reached a desired number, then the CT image data collection process is terminated, and CT images are reconstructed using the collected CT image data (step 312). The reconstruction of CT images may be performed using a technique or method known in the art. In one embodiment, the processor 54 sorts the CT image data according to the phase segment of the respiratory cycle at which it was acquired, and synchronizes the collected CT image data such that data corresponding to a given phase of a respiratory cycle are combined to reconstruct an image for that phase. When CT images for all phases of a respiratory cycle have been reconstructed, the CT images may be displayed in a sequence to form a video.

The previously described methods provide a systematic process for collecting CT image data such that a complete set of data for CT image reconstruction can be collected efficiently while considering a patient's breathing. The methods are particularly beneficial where the gantry rotation period is relatively long when compared to a respiratory cycle of the patient 16. However, the methods can also be employed for CT imaging systems with fast gantry rotation capabilities.

Figure 6:
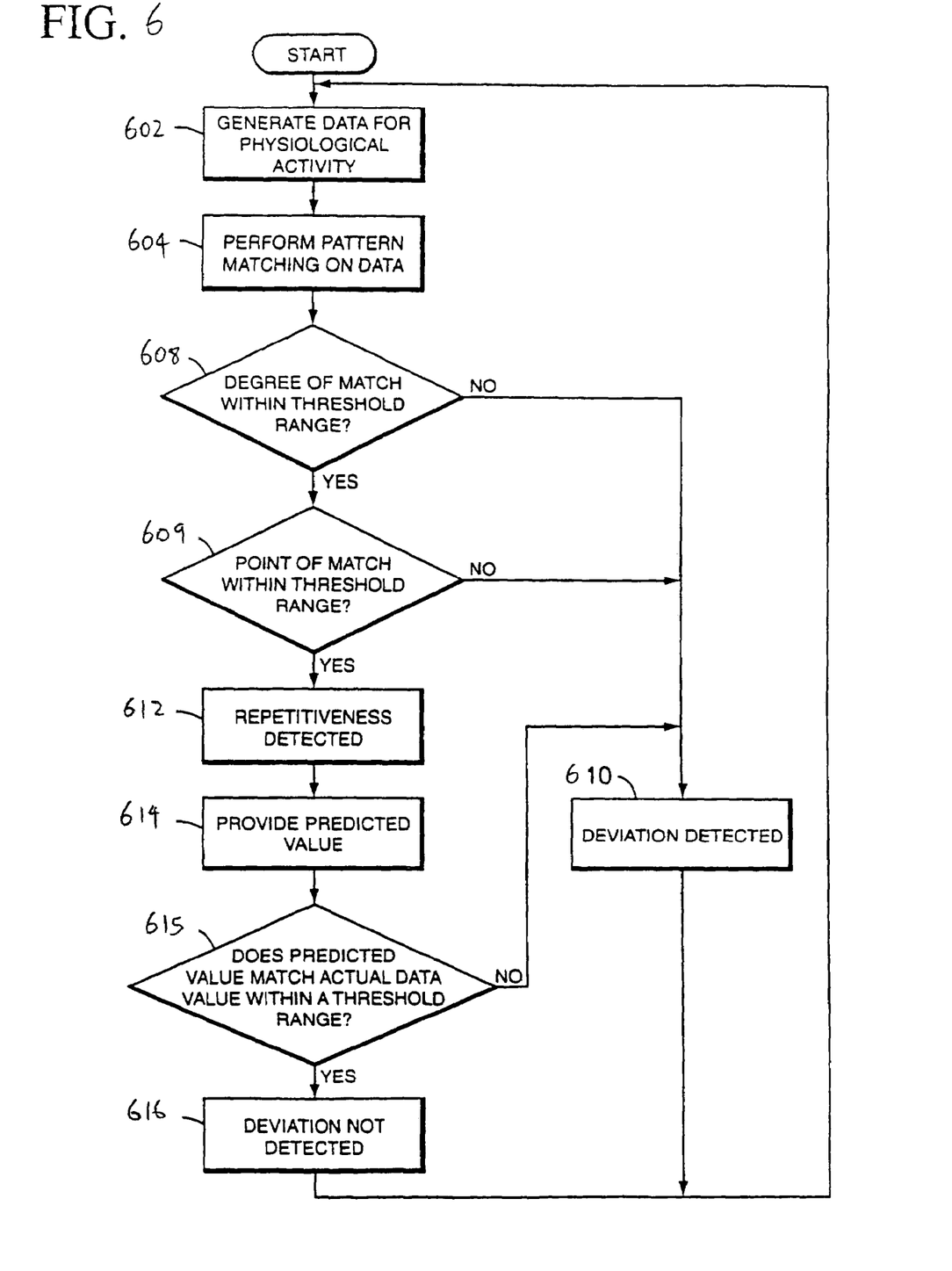
FIG. 6 is a flowchart showing a method for detecting and predictively estimating physiological movement cycles.

As discussed previously, in certain situations, it may be desirable to modulate the gantry rotation based on a predicted phase of a respiratory cycle. FIG. 6 shows a method for predictively estimating and detecting physiological movement cycles.

First, the position monitoring system 18 of FIG. 1 is employed to generate data signals representative of the physiological activity of interest (step 602). In an embodiment, the data signals comprises a stream of digital data samples that collectively form a signal wave pattern representative of the physiological movement under examination. A number of discrete measurement samples are taken for the physiological activity during a given time period. For example, in an embodiment of the invention directed towards respiratory measurement, approximately 200–210 data samples are measured for each approximately 7 second time interval.

Next, pattern matching analysis is performed against the measured data samples (step 604). In an embodiment, the most recent set of data samples for the physiological signal is correlated against an immediately preceding set of data samples to determine the period and repetitiveness of the signal. An autocorrelation function can be employed to perform this pattern matching. For each new sample point of the physiological motion or physiological monitoring sensor signal, the process computes the autocorrelation function of the last n samples of the signal, where n corresponds to approximately 1.5 to 2 signal breathing periods. The secondary peak of the autocorrelation function is then identified to determine the period and repetitiveness of the signal.

In an alternate embodiment, an absolute difference function is used instead of an autocorrelation function. Instead of secondary peak, a secondary minimum in the absolute difference is searched for. For each new sample point of the physiological motion or physiological monitoring sensor signal, the process computes the minimum absolute difference between the two sets of data over a range of overlapping data samples. The secondary minimum corresponds to the data position that best matches the recent set of data samples with the preceding set of data samples.

Yet another alternate embodiment performs a pattern matching based upon a model of the physiological activity being measured. The model is a dynamic representation of the physiological motion or physiological monitoring sensor signal for the physiological activity. The latest set of data samples is matched against the model to estimate parameters of the repetitive process.

Pattern matching using the measured physiological signal provides information regarding the degree of match, as well as a location of best match for the repetitive process. If an autocorrelation function is employed in step 604, then the relative strength of secondary peak provides a measure of how repetitive the signal is. A threshold range value is defined to provide indication of the degree of match between the two sets of data samples. If the strength of the secondary peak is within the defined threshold range (step 608), then the degree of match indicates that the signal is repetitive, and the secondary peak location provides an estimate of the signal period. If an absolute difference function is used in step 604, then the relative value of the secondary minimum provides a measure of how repetitive the signal is. If the value of the secondary minimum meets a defined threshold range (step 608), then the degree of match indicates that the signal is repetitive, and the secondary minimum location provides an estimate of the signal period.

If the correlation value of the secondary peak or secondary minimum does not meet the defined threshold range, then a deviation from the regular physiological activity is detected, thereby indicating an irregularity in the physiological movement of the patient 16 (step 610). This irregularity could result, for example, from sudden movement or coughing of the patient 16.

If the degree of match indicates repetitiveness, the point of best match is tested to determine if the period is within a reasonable range. The location of the secondary peak or secondary minimum provides an estimate of the period of the physiological activity. In an embodiment, the point of best match is compared to a threshold range (step 609). If the point of best match does not fall within the threshold range, than a deviation from regular physiological activity is detected (step 610). If the point of best match falls within the threshold range, then the signal is accepted as being repetitive (step 612).

The estimate of the period based on the point of best match can be used to predict the period and waveform parameters, such as a phase of a respiratory cycle, of the next set of data samples for the signal (step 614). Note that process actions 604, 608, and 609 test for repetitiveness based upon a plurality of data samples over a range of such samples. However, in some circumstances, a significant deviation from normal physiological movement may actually occur within the new or most recent data sample(s) being analyzed, but because the overall set of data samples indicates repetitiveness (e.g., because of averaging of absolute differences over the range of data samples being compared), process actions 604, 608, and 609 may not detect the deviation. To perform a test for rapid deviation, the predicted value from step 614 is compared with the next corresponding data sample (step 615). If the predicted value does not match the actual data sample value within a defined threshold range, then deviation is detected (step 610). If a comparison of the predicted and actual data sample values fall within the defined threshold range, then repetitiveness is confirmed, and deviation is not detected for that data sample range (step 616).

In an embodiment, the first time the process of FIG. 6 is performed, the pattern matching of step 604 is performed over the entire range of data samples. Thereafter, the pattern matching process action can be performed over a limited search interval, which is defined by the results of the prior immediate execution of the process. For example, the predicted value from step 614 can be used to define the location of the search interval for the next set of data samples.

However, if process action 608, 609, and 614 detect deviation based upon analysis of the initial search interval, then the search interval can be expanded to ensure that a deviation has actually occurred. The process of FIG. 6 can be repeated with the increased search interval to attempt to find a point of best match outside of the initial search interval. In an embodiment, this increased search interval comprises the entire range of data samples. Alternatively, the increased search interval comprises only an expanded portion of the entire range of data samples. Methods for predictively estimating and detection of physiological movement cycles have been described in U.S. patent application Ser. No. 09/893,122, referenced herein.

Figure 7A:
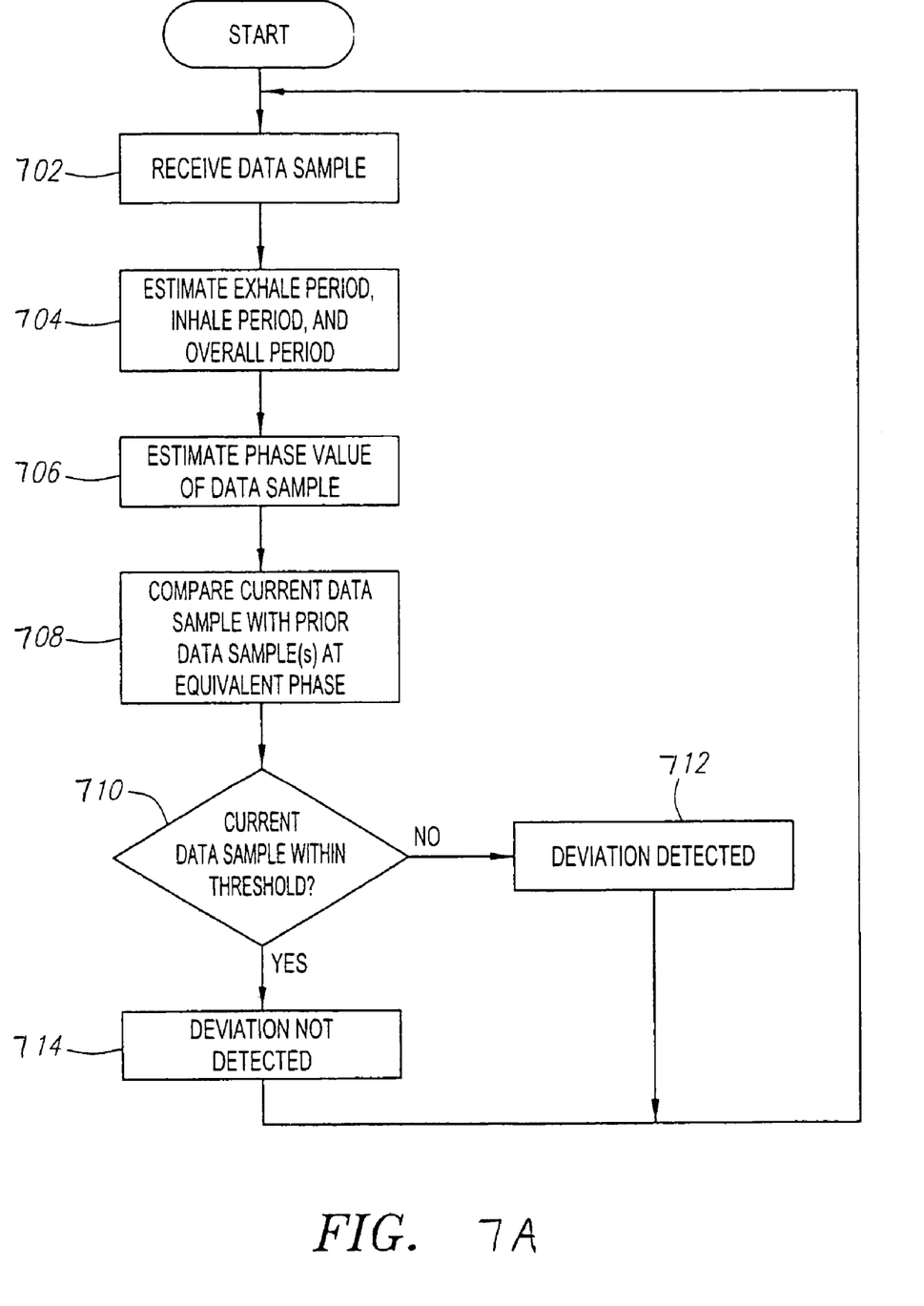
FIG. 7A shows a flowchart of a process for detecting periodicity or lack of periodicity according to an embodiment of the invention.
Figure 7B:
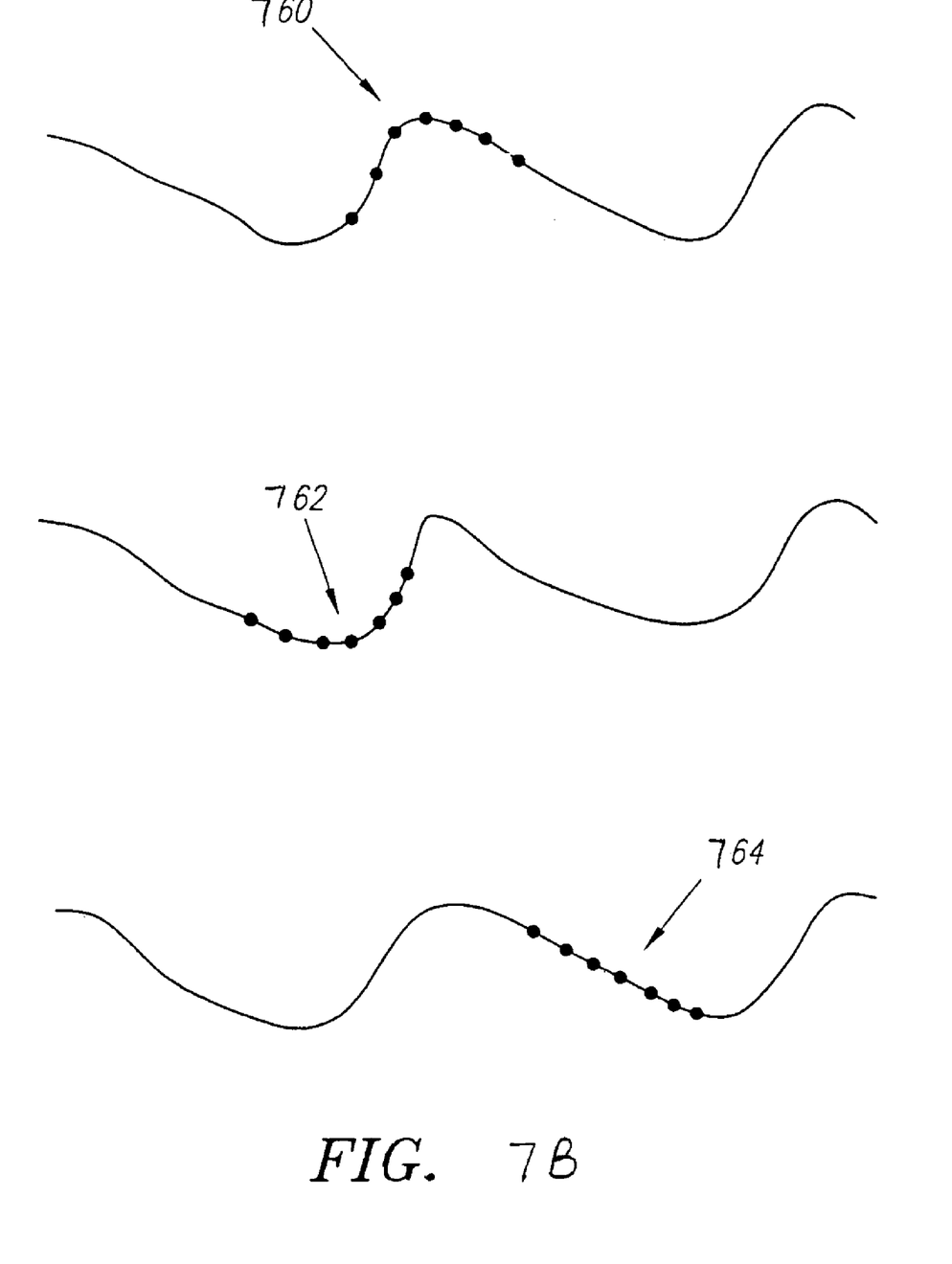
FIG. 7B illustrates sample trains according to an embodiment of the invention.
Figure 7C:
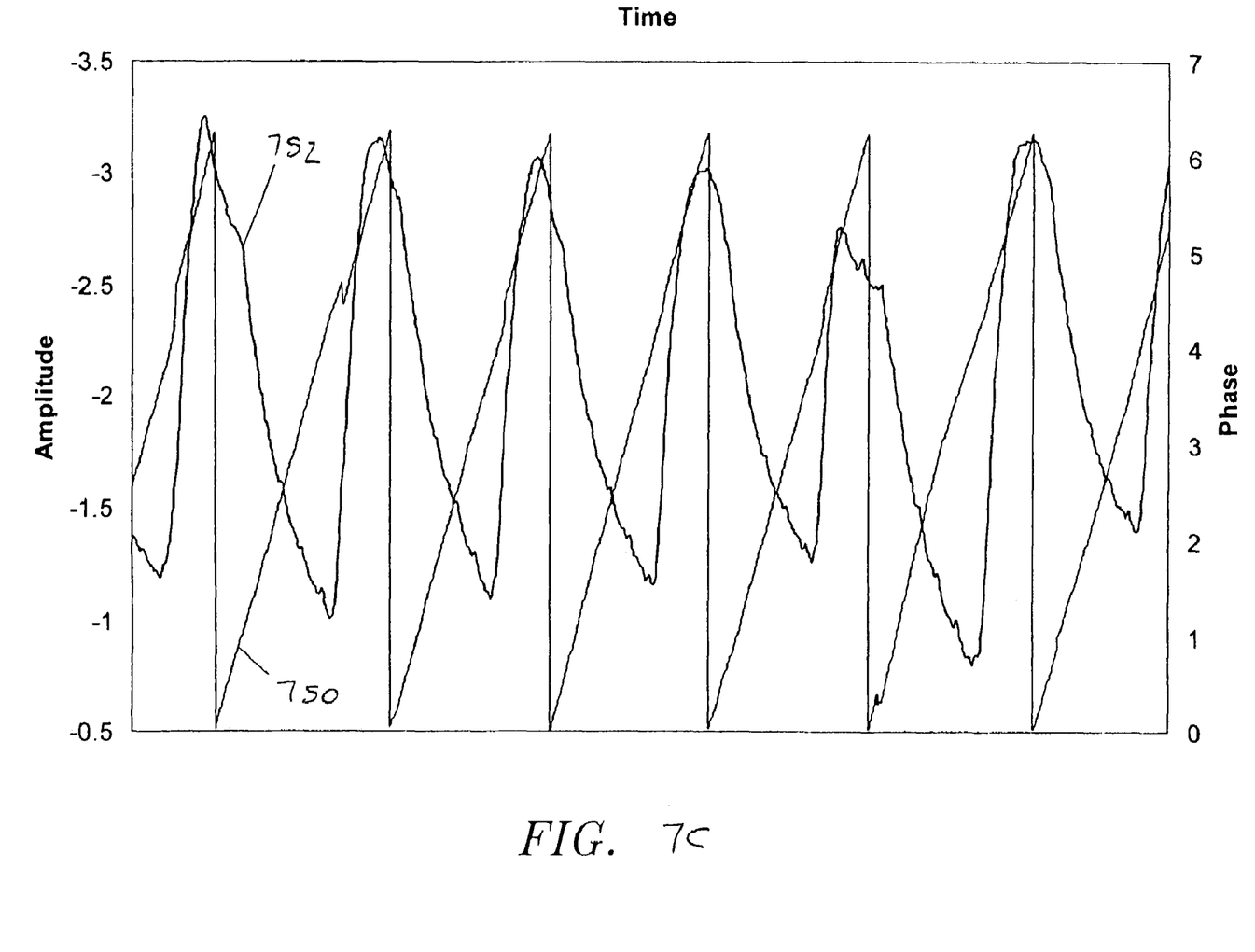
FIG. 7C is an example chart of showing phase and amplitude for a periodic signal.

FIG. 7A shows a flowchart of an alternative approach for detecting deviation from periodicity of a physiological activity. For the purposes of illustration only, and not to limit the scope of the invention, the present explanation is made with respect to the periodicity of respiration activity. This process tracks the phase of a periodic signal, and for each breathing signal sample, this approach provides an estimate of phase value (i.e., representing a degree of completion of a cycle) indicating the breathing cycle phase for the patient. In the embodiment described here, the phase angles ranges from 0 to 2 p (0 to 360 degrees) with 0 and $2\pi$ corresponding to the vicinity of inhale extreme of the respiration signal. FIG. 7C shows an example phase value chart 750 for breathing signal samples superimposed on an example of a respiration amplitude signal 752.

First, a respiration data sample is received (Step 702). For each new sample of the respiration signal, the process obtains and updates estimates of the latest inhale and latest exhale extreme values and corresponding time points of the respiration signal. These values are used to establish the latest estimates of exhale period, inhale period, and therefore T, the overall period of breathing (Step 704).

At step 706, the process estimates the phase value of the newly acquired respiration signal sample. In an embodiment, this is performed by computing the inner product of a Cosine waveform with period T (estimated at step 704) and the most recent T-seconds-long segment of the signal. This is repeated by computing the inner product with a Sine waveform of period T. These two inner products are called, respectively, the in-phase and quadrature components of the signal. The inverse Tangent of the result of dividing the quadrature value by the in-phase value provides the estimated phase for the current respiration signal sample.

Figure 7D:
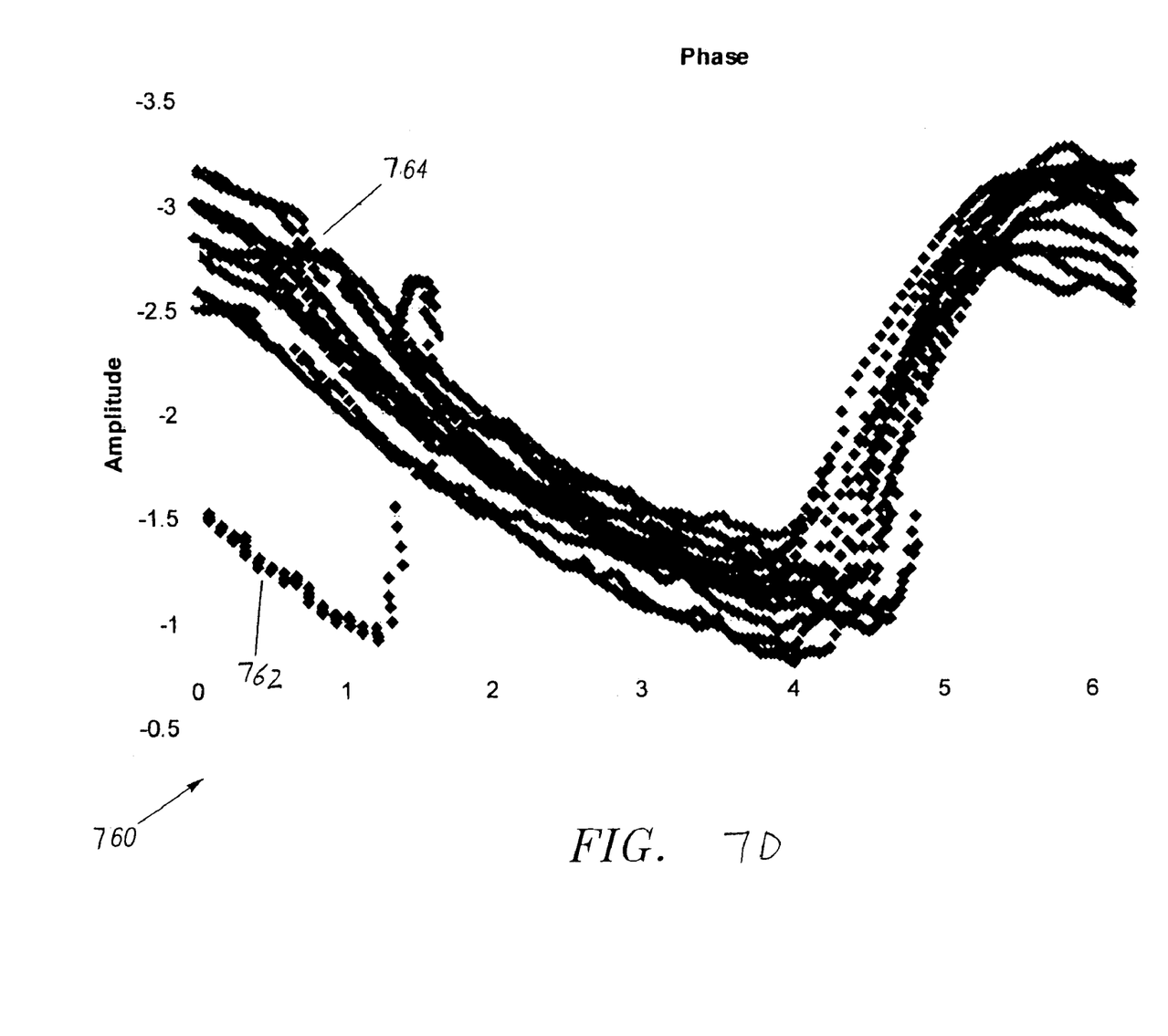
FIG. 7D shows an example of a periodic signal amplitude-phase histogram chart.

At step 708, the process compares the vector, e.g., (amplitude, phase), of the current respiration sample with previous data sample values to determine periodicity of the signal. One approach to performing this comparison step is to use a two-dimensional histogram array of signal vs. phase value that is accumulated during prior recordings of the respiration signal. FIG. 7D shows an embodiment of a 2-dimensional histogram array 760 of amplitude-phase values. Histogram array 760 is a 64×64 array of bins covering the 0 to $2\pi$ phase in the horizontal dimension and the range of respiration signal amplitude in the vertical dimension. The amplitude and estimated phase of each new sample are used to increment the corresponding bin in histogram array 760.

In an embodiment, a clustering factor determines how close the current respiration data sample vector is to the cluster of values observed so far. By comparing the amplitude-phase vector of each signal sample with the cluster of prior values in its neighborhood, the process provides a measure of periodicity for the signal. The signal is considered periodic for the current sample time when the clustering factor is above a defined threshold or tolerance level (714).

Otherwise the signal is declared non-periodic (712). One approach is to calculate the sum of the bin populations for the 8-amplitude×5-phase surrounding bins for the current data sample. This population, as a percentage of the total population of all histogram bins accumulated so far, determines the degree to which the new sample belongs to a periodic signal. By applying a threshold to this percentage value, the signal sample is declared as periodic or non-periodic. This threshold value can be set by the user as the sensitivity of the algorithm for detecting deviations from periodicity. In the example of FIG. 7D, data sample set 762 would presumably be declared as non-periodic since it substantially deviates from the general body of data sample values 764, assuming that the values in data sample set 762 cause the determined percentage value to exceed a defined threshold.

According to an embodiment, estimation of the inhale and exhale periods pursuant to step 704 of FIG. 7A begins by identifying a starting assumption of these periods. If the process is at its very beginning, or is recovering from a loss of periodicity, then nominal or default values (such as inhale period=1.6 Sec and exhale period=3.4 Sec) are used. The sum of these values is the current estimate of the physiological movement period. The approach of the present embodiment uses the most recent n samples of the signal to estimate the location and value of the minimum and maximum values, e.g., caused by breathing motion. One embodiment selects seven samples by sub-sampling the signal at intervals of ½0th of the period. The choice of seven samples makes the computational load of the interpolation process manageable, while sub-sampling allows coverage of a larger portion of the signal thus avoiding false detection of local minima and maxima due to noise. For every new sensed signal sample (not sub-sampled) the n samples selected as described above are first validated to make sure their corresponding interval includes a minimum or a maximum. This is performed by comparing the absolute difference of the two end samples of the sample train with the average of the difference of the center sample and the two end samples. One embodiment uses the test: $Abs(Y(0)-Y(6))<0.2*Abs(Y(0)+Y(6)-2*Y(3))$, to determine whether the sample train includes a minimum or a maximum. In this example the train of seven samples, $Y(0), Y(1), Y(2), Y(3), Y(4), Y(5), Y(6)$, are sub-sampled at ½0th of the of the number of samples constituting the current estimate of one period. If the result of this test is positive, curve fitting to the samples is performed. One embodiment fits a quadratic curve to the middle five points of the seven-point sample train. The location and value of the minimum or maximum value of this curve is computed using interpolation. Also at this point, it is determined whether the estimated point is a minimum or a maximum by comparing the end samples of the train with the middle sample. The estimated location of the minimum or maximum points are added to their respective accumulator variables for later averaging.

The above process is repeated with the next sensed signal sample until the procedure encounters the first sample for which the above test result is negative. This is an indication that the run of points for which a minimum or maximum can be estimated has ended. At this point the accumulator variables are divided by the number of points in the run to obtain the average location and value from the run.

The process continues by repeating the above test on the sample-train preceding every new sensed signal sample. Once the test result is positive the averaging process described above will start again. FIG. 7B shows three examples of sample trains; sample train 760 includes a local maximum; sample train 762 includes a local minimum; and, sample train 764 includes neither a maximum nor a minimum.

This method estimates the local minimum or maximum location at a point in time that is later than the actual position of the maximum or minimum by the length of the sample train. The current estimate of the inhale or exhale period is updated at this point in time. For inhale period, for example, this is performed by subtracting the latest maximum position from the latest minimum position in time. These estimates are used to update the current value of the total period.

The above method for detecting deviation from periodicity of a physiological activity has been described in U.S. patent application Ser. No. 10/678,741, the entire disclosure of which is expressly incorporated by reference herein.

The embodiments described herein provides a tool for measuring the periodicity of the respiration signal, thus allowing detection of deviation from normal physiological movement, e.g., deviation from normal breathing caused by a patient coughing or moving. This can be used during therapy, imaging, and interventional procedures that is facilitated or require monitoring of normal patient movement. In addition, the knowledge of the phase of the physiological activity allows predictive or prospective triggering of image acquisition or the onset of radiation therapy beam in situations where these systems respond after a known delay.

Computer System Architecture

Figure 8:
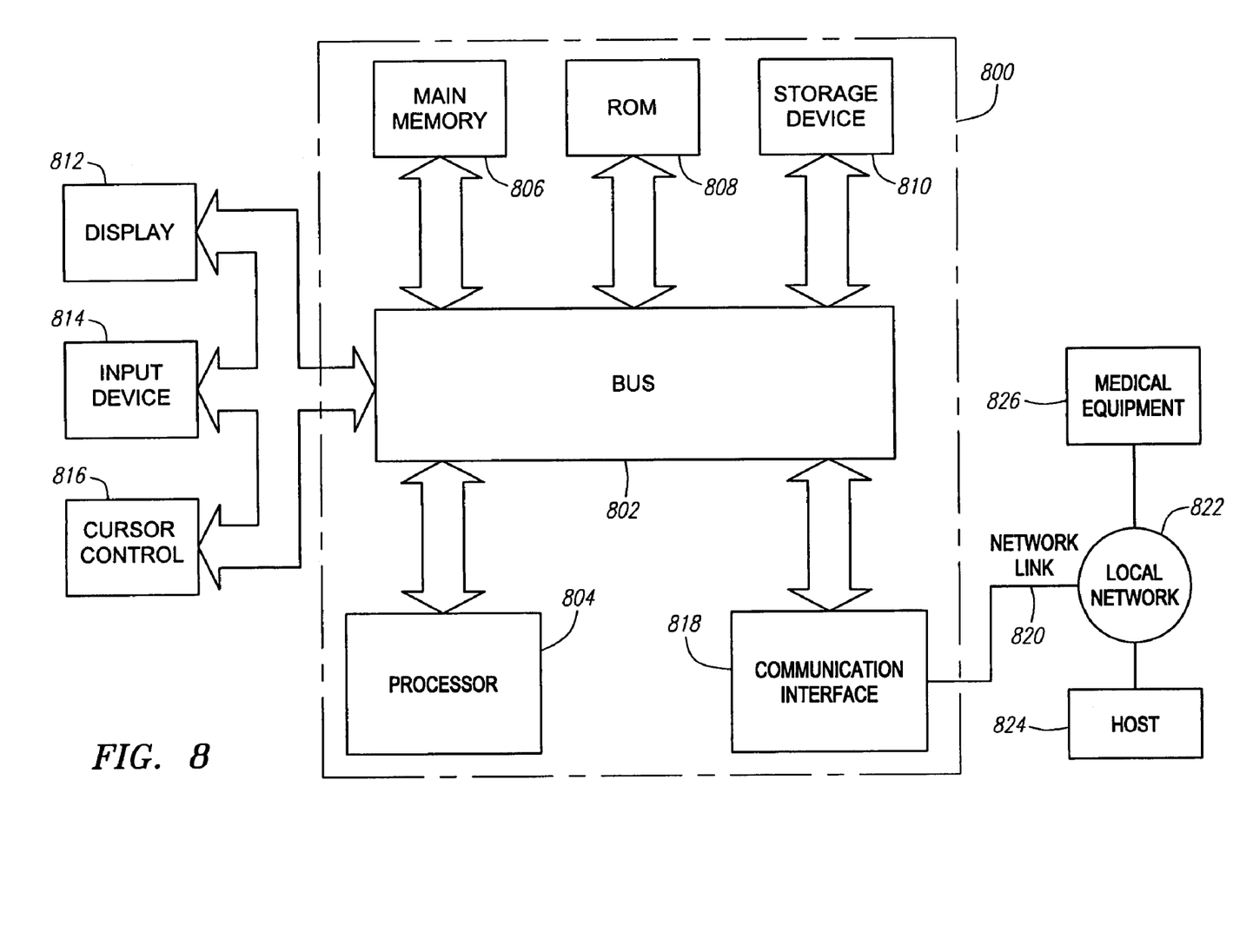
FIG. 8 is a diagram of a computer hardware system with which embodiments of the present invention can be implemented.

FIG. 8 is a block diagram that illustrates an embodiment of a computer system 800 upon which an embodiment of the invention may be implemented. Computer system 800 includes a bus 802 or other communication mechanism for communicating information, and a processor 804 coupled with the bus 802 for processing information. The processor 804 may be an example of the processor 54, or alternatively, an example of a component of the processor 54, of FIG. 1. The computer system 800 also includes a main memory 806, such as a random access memory (RAM) or other dynamic storage device, coupled to the bus 802 for storing information and instructions to be executed by the processor 804. The main memory 806 also may be used for storing temporary variables or other intermediate information during execution of instructions to be executed by the processor 804. The computer system 800 further includes a read only memory (ROM) 808 or other static storage device coupled to the bus 802 for storing static information and instructions for the processor 804. A data storage device 810, such as a magnetic disk or optical disk, is provided and coupled to the bus 802 for storing information and instructions.

The computer system 800 may be coupled via the bus 802 to a display 87, such as a cathode ray tube (CRT), for displaying information to a user. An input device 814, including alphanumeric and other keys, is coupled to the bus 802 for communicating information and command selections to processor 804. Another type of user input device is cursor control 816, such as a mouse, a trackball, or cursor direction keys for communicating direction information and command selections to processor 804 and for controlling cursor movement on display 87. This input device typically has two degrees of freedom in two axes, a first axis (e.g., x) and a second axis (e.g., y), that allows the device to specify positions in a plane.

The invention is related to the use of computer system 800 for collecting and processing image data. According to one embodiment of the invention, such use is provided by computer system 800 in response to processor 804 executing one or more sequences of one or more instructions contained in the main memory 806. Such instructions may be read into the main memory 806 from another computer-readable medium, such as storage device 810. Execution of the sequences of instructions contained in the main memory 806 causes the processor 804 to perform the process steps described herein. One or more processors in a multi-processing arrangement may also be employed to execute the sequences of instructions contained in the main memory 806. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to the processor 804 for execution. Such a medium may take many forms, including but not limited to, non-volatile media, volatile media, and transmission media. Non-volatile media includes, for example, optical or magnetic disks, such as the storage device 810. Volatile media includes dynamic memory, such as the main memory 806. Transmission media includes coaxial cables, copper wire and fiber optics, including the wires that comprise the bus 802. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a is FLASH-EPROM, any other memory chip or cartridge, a carrier wave as described hereinafter, or any other medium from which a computer can read.

Various forms of computer-readable media may be involved in carrying one or more sequences of one or more instructions to the processor 804 for execution. For example, the instructions may initially be carried on a magnetic disk of a remote computer. The remote computer can load the instructions into its dynamic memory and send the instructions over a telephone line using a modem. A modem local to the computer system 800 can receive the data on the telephone line and use an infrared transmitter to convert the data to an infrared signal. An infrared detector coupled to the bus 802 can receive the data carried in the infrared signal and place the data on the bus 802. The bus 802 carries the data to the main memory 806, from which the processor 804 retrieves and executes the instructions. The instructions received by the main memory 806 may optionally be stored on the storage device 810 either before or after execution by the processor 804.

The computer system 800 also includes a communication interface 818 coupled to the bus 802. The communication interface 818 provides a two-way data communication coupling to a network link 820 that is connected to a local network 822. For example, the communication interface 818 may be an integrated services digital network (ISDN) card or a modem to provide a data communication connection to a corresponding type of telephone line. As another example, the communication interface 818 may be a local area network (LAN) card to provide a data communication connection to a compatible LAN. Wireless links may also be implemented. In any such implementation, the communication interface 818 sends and receives electrical, electromagnetic or optical signals that carry data streams representing various types of information.

The network link 820 typically provides data communication through one or more networks to other devices. For example, the network link 820 may provide a connection through local network 822 to a host computer 824 or to medical equipment 826 such as a radiation beam source or a switch operatively coupled to a radiation beam source. The data streams transported over the network link 820 can comprise electrical, electromagnetic or optical signals. The signals through the various networks and the signals on the network link 820 and through the communication interface 818, which carry data to and from the computer system 800, are exemplary forms of carrier waves transporting the information. The computer system 800 can send messages and receive data, including program code, through the network(s), the network link 820, and the communication interface 818.

Although the embodiments of the systems and methods have been described with reference to generating CT images based on breathing synchronization, it should be understood that the systems and methods may also be implemented to generate CT images based on synchronization of cardiac motion or other physiological motions. In addition, although the gantry 12 has been described as making a 360° rotation around the patient 16 during image data acquisition, such needs not be the case. For example, if a full cone detector is used, the system 10 may acquire data while the gantry 12 rotates 180° plus the angle of the beam pattern. Other angles of rotation may also be used, depending on the particular system being employed. Furthermore, instead of a CT procedure, the above described techniques or similar techniques can be implemented in a laminar tomography procedure, a MRI procedure, a PET procedure, or other imaging procedures, in which a plurality of image data is desired to be generated. As such, the gantry 12 should not be limited to a rotatable structure as described previously, and could have other configurations, such as a sliding or translating configuration, depending on the particular application or procedure.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. For example, the operations performed by the processor 54 can be performed by any combination of hardware and software within the scope of the invention, and should not be limited to particular embodiments comprising a particular definition of "processor". The specification and drawings are, accordingly, to be regarded in an illustrative rather than restrictive sense. The present inventions are intended to cover alternatives, modifications, and equivalents, which may be included within the spirit and scope of the present inventions as defined by the claims.

What is claimed:

1. A method for collecting computed tomography (CT) image data, comprising:
   determining a number of intervals N into which a respiratory cycle is to be divided, wherein the number of intervals N is greater than one;
   determining a number of respiratory cycle(s) M to be covered in one gantry rotation; and
   rotating a gantry to collect at least M x N sets of CT image data of at least a portion of a patient, wherein each set of the CT image data corresponds to a phase of a respiratory cycle.

2. The method of claim 1, further comprising repeating the step of rotating until the number of gantry rotation is at least N.

3. The method of claim 2, wherein the repeating comprises rotating the gantry at a phase that is offset from that of the previous gantry rotation.

4. The method of claim 3, wherein the offset phase is 360°/(M×N) or less.

5. The method of claim 3, wherein the offset phase is 180°/(M×N) or less.

6. The method of claim 1, wherein the rotating comprises causing the gantry to rotate at a constant speed.

7. The method of claim 1, wherein the rotating comprises causing the gantry to rotate at a variable speed.

8. The method of claim 1, further comprising determining a breathing phase of the patient.

9. The method of claim 8, wherein the rotating comprises causing the gantry to rotate at a speed based on the breathing phase of the patient.

10. The method of claim 8, further comprising adjusting the speed of the gantry rotation based on the determined breathing phase of the patient.

11. The method of claim 10, wherein the adjusting comprises changing the speed of the gantry rotation by a prescribed amount until a gantry phase matches with a corresponding breathing phase of the patient.

12. The method of claim 10, further comprising determining a difference between a gantry phase and the determined breathing phase, wherein the adjusting comprises changing the speed of the gantry rotation in response to the difference.

13. The method of claim 10, further comprising:
estimating a next breathing phase of the patient based on the determined phase of the patient; and
wherein the adjusting comprises changing the speed of the gantry rotation based on the estimated next breathing phase.

14. The method of claim 1, further comprising generating motion data associated with a breathing of the patient.

15. The method of claim 14, further comprising synchronizing the collected CT image data and the motion data to a common time base.

16. The method of claim 1, further comprising sorting the collected sets of CT image data such that at least two of the sets of CT image data that correspond to a same phase of a respiratory cycle are grouped for CT image reconstruction.

17. A computer readable medium having a set of stored instructions, the execution of which causes a process to be performed, the process comprising:
determining a number of intervals N into which a respiratory cycle is to be divided, wherein the number of intervals N is greater than one;
determining a number of respiratory cycle(s) M to be covered in one gantry rotation; and
rotating a gantry to collect at least M×N sets of CT image data of at least a portion of a patient, wherein each set of the CT image data corresponds to a phase of a respiratory cycle.

18. The computer readable medium of claim 17, wherein the process further comprises repeating the step of rotating until the number of gantry rotation is at least N.

19. The computer readable medium of claim 18, wherein the repeating comprises rotating the gantry at a phase that is offset from that of the previous gantry rotation.

20. The computer readable medium of claim 19, wherein the offset phase is 360°/(M×N) or less.

21. The computer readable medium of claim 19, wherein the offset phase is 180°/(M×N) or less.

22. The computer readable medium of claim 17, wherein the rotating comprises causing the gantry to rotate at a constant speed.

23. The computer readable medium of claim 17, wherein the rotating comprises causing the gantry to rotate at a variable speed.

24. The computer readable medium of claim 17, wherein the process further comprising determining a breathing phase of the patient.

25. The computer readable medium of claim 24, wherein the rotating comprises causing the gantry to rotate at a speed based on the breathing phase of the patient.

26. The computer readable medium of claim 24, wherein the process further comprising adjusting the speed of the gantry rotation based on the determined breathing phase of the patient.

27. The computer readable medium of claim 26, wherein the adjusting comprises changing the speed of the gantry rotation by a prescribed amount until a gantry phase matches with a corresponding breathing phase of the patient.

28. The computer readable medium of claim 26, wherein the process further comprising determining a difference between a gantry phase and the determined breathing phase, wherein the adjusting comprises changing the speed of the gantry rotation in response to the difference.

29. The computer readable medium of claim 26, wherein the process further comprising:
estimating a next breathing phase of the patient based on the determined phase of the patient; and
wherein the adjusting comprises changing the speed of the gantry rotation based on the estimated next breathing phase.

30. The computer readable medium of claim 17, wherein the process further comprising generating motion data associated with a breathing of the patient.

31. The computer readable medium of claim 30, wherein the process further comprising synchronizing the collected CT image data and the motion data to a common time base.

32. The computer readable medium of claim 17, wherein the process further comprising sorting the collected sets of CT image data such that at least two of the sets of CT image data that correspond to a same phase of a respiratory cycle are grouped for CT image reconstruction.

33. A system for collecting computed tomography (CT) image data, comprising:
means for determining a number of intervals N into which a respiratory cycle is to be divided, wherein the number of intervals N is greater than one;
means for determining a number of respiratory cycle(s) M to be covered in one gantry rotation; and
means for rotating a gantry to collect at least M×N sets of CT image data of at least a portion of a patient, wherein each set of the CT image data corresponds to a phase of a respiratory cycle.

34. The system of claim 33, wherein the means for rotating the gantry rotates the gantry at least N times.

35. The system of claim 34, wherein the means for rotating causes the gantry to rotate at a phase that is offset from that of the previous gantry rotation.

36. The system of claim 35, wherein the offset phase is 360°/(M×N) or less.

37. The system of claim 35, wherein the offset phase is 180°/(M×N) or less.

38. The system of claim 33, wherein the means for rotating causes the gantry to rotate at a constant speed.

39. The system of claim 33, wherein the means for rotating causes the gantry to rotate at a variable speed.

40. The system of claim 33, further comprising means for determining a breathing phase of the patient.

41. The system of claim 40, wherein the means for rotating comprises causing the gantry to rotate at a speed based on the breathing phase of the patient.

42. The system of claim 40, further comprising means for adjusting the speed of the gantry rotation based on the determined breathing phase of the patient.

43. The system of claim 42, wherein the means for adjusting comprises means for changing the speed of the gantry rotation by a prescribed amount until a gantry phase matches with a corresponding breathing phase of the patient.

44. The system of claim 42, further comprising means for determining a difference between a gantry phase and the determined breathing phase, wherein the means for adjusting comprises means for changing the speed of the gantry rotation in response to the difference.

45. The system of claim 42, further comprising:
means for estimating a next breathing phase of the patient based on the determined phase of the patient; and
wherein the means for adjusting comprises means for changing the speed of the gantry rotation based on the estimated next breathing phase.

46. The system of claim 33, further comprising means for generating motion data associated with a breathing of the patient.

47. The system of claim 46, further comprising means for synchronizing the collected CT image data and the motion data to a common time base.

48. The system of claim 33, further comprising means for sorting the collected sets of CT image data such that at least two of the sets of CT image data that correspond to a same phase of a respiratory cycle are grouped for CT image reconstruction.

49. A method for generating a computed tomography (CT) image, comprising:
collecting data samples representative of a physiological movement of a patient due to breathing;
determining a number of intervals N into which a breathing cycle of the patient is to be divided, wherein the number of intervals N is greater than one;
rotating a gantry at least N times to acquire image data of at least a part of the patient;
gathering image data acquired at a same phase of a breathing cycle; and
generating a CT image using the gathered image data.

50. The method of claim 49, further comprising controlling a speed of the gantry based on the data samples.

51. The method of claim 49, wherein the generating the CT image comprises constructing a volumetric image.

52. A computer readable medium having a set of stored instructions, the execution of which causes a process to be performed, the process comprising:
collecting data samples representative of a physiological movement of a patient due to breathing;
determining a number of intervals N into which a breathing cycle of the patient is to be divided, wherein the number of intervals N is greater than one;
rotating a gantry at least N times to acquire image data of at least a part of the patient;
gathering image data acquired at a same phase of a breathing cycle; and
generating a CT image using the gathered image data.

53. The computer readable medium of claim 52, wherein the process further comprising controlling a speed of the gantry based on the data samples.

54. The computer readable medium of claim 52, wherein the generating the CT image comprises constructing a volumetric image.

55. A system for generating a computed tomography (CT) image, comprising:
means for collecting data samples representative of a physiological movement of a patient due to breathing;
a processor for receiving an input representative of a number of intervals N into which a breathing cycle of the patient is to be divided, wherein the number of intervals N is greater than one; and
a gantry rotation control for rotating a gantry at least N times to acquire image data of at least a part of the patient.

56. The system of claim 55, wherein the processor is configured for gathering image data acquired at a same phase of a breathing cycle.

57. The system of claim 55, wherein the gantry rotation control is configured for controlling a speed of the gantry based on the data samples.

* * * * *